United States Patent
Dendy et al.

[11] Patent Number: 6,142,303
[45] Date of Patent: Nov. 7, 2000

[54] INTERIM STORAGE AND PERMANENT DISPOSAL OF MEDICAL SHARPS

[75] Inventors: Joe A. Dendy; Mark T. Rodgers; Lucas T. Dobrzanski, all of Bakersfield, Calif.

[73] Assignee: Earth-Shield Incorporated, Bakersfield, Calif.

[21] Appl. No.: 09/187,533

[22] Filed: Nov. 5, 1998

[51] Int. Cl.[7] .................................................. B65D 69/00
[52] U.S. Cl. ........................ 206/568; 206/366; 206/370; 215/263; 220/908; 106/697; 106/724; 106/823
[58] Field of Search .................................. 206/205, 210, 206/219, 366, 370, 568; 220/908; 106/697, 698, 724, 823; 588/252; 215/263, 274

[56] References Cited

U.S. PATENT DOCUMENTS

| | | | |
|---|---|---|---|
| 2,017,800 | 10/1935 | Hilgenberg | 206/568 X |
| 3,590,989 | 7/1971 | Wittwer | 206/568 |
| 3,837,872 | 9/1974 | Conner | 588/252 |
| 3,876,067 | 4/1975 | Schwartz . | |
| 3,972,723 | 8/1976 | Balle et al. | 106/774 X |
| 4,171,226 | 10/1979 | Hesselgren | 106/697 X |
| 4,502,606 | 3/1985 | Shillington et al. | 215/774 |
| 4,816,307 | 3/1989 | Honeycutt | 206/366 X |
| 4,860,888 | 8/1989 | Keith | 206/568 X |
| 4,919,569 | 4/1990 | Wittenzelliner . | |
| 4,946,037 | 8/1990 | Keith | 206/568 X |
| 5,038,929 | 8/1991 | Kubofcik | 206/210 |
| 5,172,808 | 12/1992 | Bruno | 206/366 |
| 5,322,165 | 6/1994 | Melker et al. | 206/366 |
| 5,378,279 | 1/1995 | Conroy | 106/724 X |
| 5,584,926 | 12/1996 | Borgholm et al. | 106/823 X |
| 5,658,380 | 8/1997 | Dillenbeck, III | 106/823 |
| 5,674,175 | 10/1997 | Bailey . | |
| 5,772,059 | 6/1998 | McCord | 215/230 X |
| 5,810,920 | 9/1998 | Ueshima et al. | 106/697 |

*Primary Examiner*—Bryon P. Gehman
*Attorney, Agent, or Firm*—Donald D. Mon

[57] ABSTRACT

Apparatus and method for the interim sanitary storage of medical sharps and subsequent inurnment of them to a condition acceptable in commercial landfills. A receptacle contains dry calcium hypochlorite to sanitize sharps that are placed in the reception. It has a removable closure cap to admit the sharps. A supply container contains cementitious material to which water is added, and then poured into the receptacle to envelop the sharps. A permanent lock is applied to the receptacle cap to prevent further access or escape of the sharps which are encapsulated in the resulting cementitious urn.

6 Claims, 1 Drawing Sheet

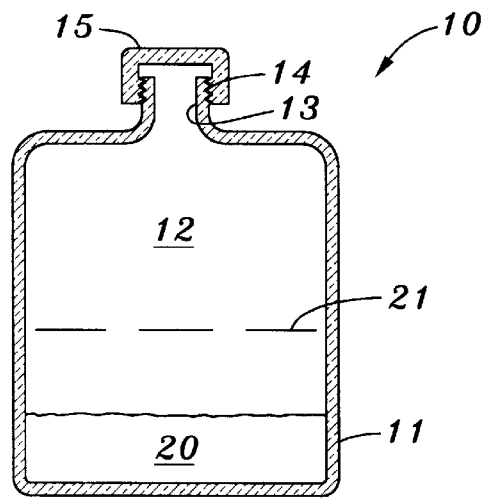
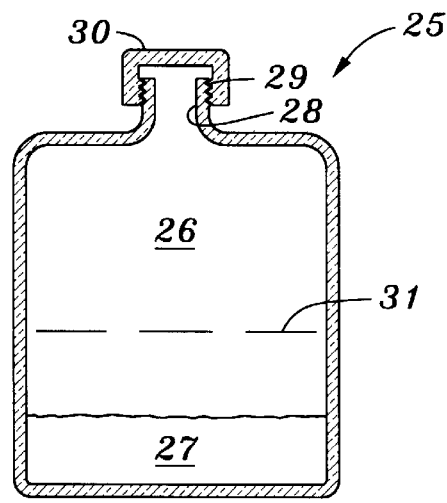
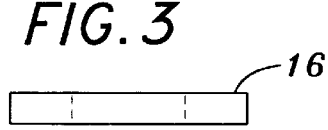
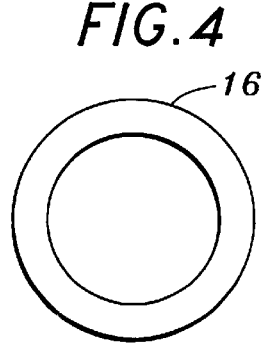
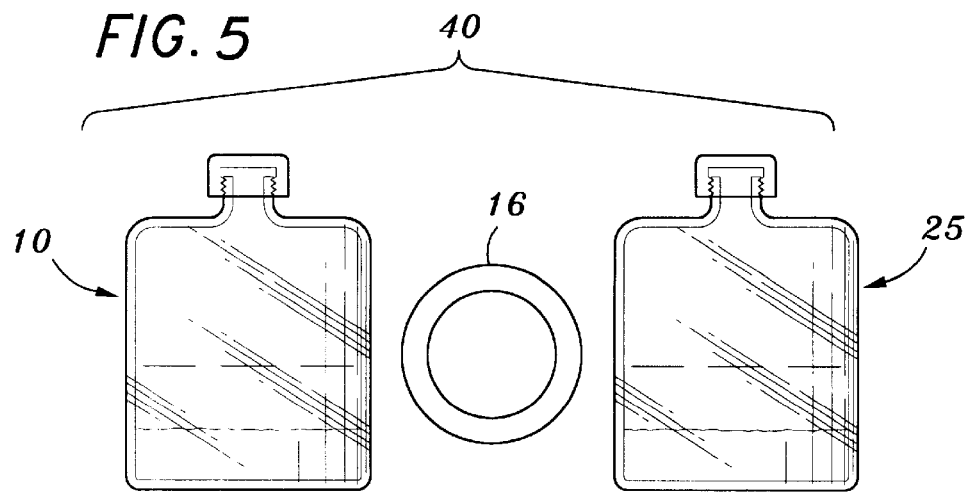

INTERIM STORAGE AND PERMANENT DISPOSAL OF MEDICAL SHARPS

FIELD OF THE INVENTION

The interim storage of used medical sharps and their permanent encapsulation in an ecological condition acceptable to long-term landfills.

BACKGROUND OF THE INVENTION

The term for purposes here, "medical sharps," refers to used medical and surgical devices intended to be disposed of after use instead of being sterilized for re-use. These include items such as needles, syringes, scalpels and scalpels blades which have sharp edges that can harm a person, especially when they are contaminated with microorganisms such as viruses and bacteria.

Many medical offices, clinics and hospitals generate used medical sharps which immediately after usage must be put in a safe place and ultimately disposed of. Locations having a very high rate of generation of these objects usually have a collection system in which the sharps are placed in a closed container that is collected and discharged at a separated collection point where a very large number of sharps are gathered and sent elsewhere for ultimate disposal.

Such arrangements may be suitable for large sites, but are not satisfactory for places where the generation of sharps is less frequent. The presence of these larger collection systems in the office or clinic becomes a matter of continuous concern because of the risk of physical contact that might penetrate the skin, and of contamination by microorganisms which they might carry.

This is an active field because of the serious concerns which it involves. It is to be expected that many efforts have been made to solve the problems. Generally they are addressed to the containment of sharps, often involving trap-like structures and sanitizing liquids. In theory these should all be satisfactory, but generally they bring with them their own problems.

For example, systems which use liquids to destroy microorganisms in a container which receives the sharps present the risk of spilling or of release from a broken or tipped over container. Then when the container is finally filled, the problem arises of what to do with it. A landfill is the preferred destination, but those are steadily restricting the standards of what they will accept. Anything of this type that includes a liquid, no matter how strong the container, is likely to be rejected, especially if it may contain hazardous or dangerous materials.

So there results a need for a receptacle for sharps which receptacle contains materials that have the capacity to destroy microorganisms, and are safe in case of a spill in the office. This means a solid material, rather than a liquid. While in use as a receptacle for post-use sharps, over a period that may last as long as a year, it should not have a disagreeable odor when opened, nor emit noxious gases.

Then, when the receptacle is to be converted to a permanent urn, the composition surrounding the sharps should be a stable solid material which is self shape retaining and which consists entirely of materials that are acceptable in landfills that do not accept hazardous materials, thereby eliminating any need for incineration of the sharps. In some arrangements the urn's composition may even result in the decomposition of the sharps over a long period of time.

Additionally, it is necessary that the receptacle, now an urn, remain unruptured after the final encapsulation of the sharps because landfills will not accept broken containers of this sort or accept containers that break easily. Excessive heat might weaken or damage the receptacle during a curing process to be described herein. Accordingly, self-contained means can advantageously be provided to maintain the curing temperature at a low level that does not degrade the container, and the container must be strong enough to resist strong forces such as are exerted by a compactor in a landfill.

This invention provides a receptacle and substances which accomplish these objectives.

BRIEF DESCRIPTION OF THE INVENTION

A receptacle with a closed wall forms a cavity which is to receive sharps for interim storage and final disposal. An opening through its wall admits the sharps and has a closure which is removable until final disposition, at which time a permanent lock is applied.

According to this invention, the receptacle is partially filled with a solid granular or powdery material having the property of gradually emitting a gas destructive of microorganisms. The presently preferred substance is calcium hypochlorite which has good stability over a period of time, but does gradually break down to emit useful quantities of chlorine gas that are destructive of microorganisms. This effect is even more pronounced when a wet or damp sharp is placed in it.

According to this invention, a supply container is provided whose purpose is to supply to the receptacle a cementitious slurry which, when poured into the receptacle and shaken with the contents of the receptacle will set (cure) to form a solid encapsulation that is fully contained in the receptacle. Should the receptacle later be breached or broken, the solidified mass will remain intact. The microorganisms in it will have been destroyed both by the material originally in the receptacle, and by the alkalinity of the slurry.

In addition, the supply container holds a chemical reducing agent, provided to reduce any remaining calcium hypochlorite, thereby eliminating any further generation of gases. The reducing agent also takes away hazardous characteristics of the calcium hypochlorite, which characteristics would prevent disposal in a non-hazardous landfill.

According to a preferred but optional feature of the invention, a temperature-reducing additive is provided which has a negative heat of solution, whereby to counter some of the heat produced by calories developed in the setting and chemical reduction process. The presently preferred additive is potassium chloride.

The above and other features of this invention will be fully understood from the following detailed description and the accompanying drawings, in which:

BRIEF DESCRIPTION OF THE DRAWINGS

FIG. 1 is an axial cross-section of a closed receptacle according to this invention;

FIG. 2 is an axial cross-section of a closed supply container according to this invention;

FIG. 3 is a side view of a locking ring for use with the receptacle of FIG. 1;

FIG. 4 is a top view of FIG. 3; and

FIG. 5 shows the entire kit.

DETAILED DESCRIPTION OF THE INVENTION

A receptacle 10 for use with this invention has a wall 11 which forms an internal cavity 12. A port 13 through the top of the container has an externally threaded neck 14 to receive a cap 15. It is preferred that cap 15 be of a typical ratchet-type child-safe type which is intended to limit access, and to be less likely to loosen in the event the container is knocked over. This safety feature is optional.

A rigid locking ring 16, shown separately in FIG. 3 is kept available but in a place where it is unlikely to be attached to the receptacle until the continuing use of this receptacle is concluded. At such time, it will be placed around the neck between the cap and the receptacle when a permanent closure is required. It is not compressible and will prevent the cap from being depressed after the cap is tightened. Then the ratchet cannot thereafter engage and the cap cannot be unthreaded from the neck.

A suitable quantity of dry solid material 20 is added to the receptacle, into which the sharps will be placed. The level to which the solid material is added leaves sufficient open volume even after all of the sharps are placed in the receptacle, that the sharps and a slurry to be described can be received and shaken together with the solid material and sharps. The presently preferred solid material is dry calcium hypochlorite—Ca(OCl)2 in granule or powder condition. Sharps can be dropped into the container up to a sharps fill line 21 on the wall of the receptacle.

A supply container 25 has a wall which forms an internal cavity 26 to store a desired amount of the solid reagents and materials 27 needed for the final solidification, encapsulation and disposition of the sharps. It has a port 28 with an externally threaded neck 29. Neck 29 receives a removable cap 30 that forms a closure to contain the materials.

A reference line 31 is provided to show the level of water to be added, and still leave room for shaking the water and solid material to form a slurry.

According to this invention the materials in the supply container are kept dry until they are to be used. They are for the purpose of reducing any remaining hypochlorite in the receptacle, for creating a slurry with a pH above 11.5, for forming a cementitious body encapsulating the sharps, and for reducing the temperature generated by the curing of the cements and by reduction of the hypochlorite. The receptacle and the supply container are sold as a kit so the substances in them will be present when the need for them arises. The materials in the supply container are:

Portland cement and pumice are provided to form a cementitious body.

Sodium sulfite (NA2SO3) is provided as a reducing agent.

Potassium chloride is provided for temperature reduction. All are provided for creating a slurry with a pH above 11.5.

The use of this product is straightforward. Sharps are dropped into the receptacle, and the cap is replaced after each insertion. A very faint bleach odor will be detected, which is neither dangerous nor objectionable. Because chlorine is a heavier gas, it is unlikely to escape the receptacle, and likely to be retained in it. It is a "friendly" smell, and indicates that chlorine is present to destroy the microorganisms, which in fact it does.

When sufficient sharps have been inserted into the receptacle, or when the desired maximum shelf life of the hypochlorite has passed, the supply container and its contents will be used. The half life of the hypochlorite in the receptacle is about 2 years. A sensible shelf life is about one year.

In the supply container, water is added to line 31, and the container is closed and shaken vigorously for about thirty seconds. This will activate these materials and form a slurry.

This slurry is promptly poured from the supply container into the receptacle. It is closed, and is vigorously shaken for about thirty seconds to thoroughly mix the contents. The supply container can be separately disposed of as ordinary trash.

Now, in addition to the setting of the cement in the receptacle, the following reaction occurs:

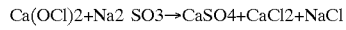

This is in addition to the curing of the cement and the formation of the matrix with the pumice. The potassium chloride takes no part in the reaction. When used, and it need not always be used, it merely accepts calories with its negative heat of solution to keep the temperature at a maximum of about 125 degree F. which is best not to exceed so that the integrity and safe handling of the plastic container will not be compromised.

After about 48 hours, the mass in the receptacle will have been set and cured. The ring 16 will have been placed around the receptacle neck, and the receptacle cap will then have been closed. The receptacle, now an urn, is permanently closed and ready to go to the landfill for permanent disposal.

This material qualifies for long term disposal in a non-hazardous landfill.

The material of the receptacle itself is preferably non-biodegradable, impermeable and strong, for example high density polypropylene. The supply container may be an ordinary polyethylene bottle. Its disposal represents no problem.

A convenient volume for the receptacle is about 2 quarts. About 50 gm of calcium hypochlorite will be added, which after the sharps are inserted to capacity, leaves a volume of about 1.5 quarts as open volume in which to receive the slurry.

A convenient volume for the supply container is about 1 gallon. It will be filled about as follow:

| | |
|---|---|
| Sodium Sulfite: | 70–90 preferably 79 gm |
| Potassium Chloride: | 150–250 preferably 200 gm |
| Pumice: | 500–600 gm preferably 570 gm |
| Portland Cement: | 800–1,000 gm preferably 920 gm |

About 1,300 ml (37 fl oz) of water will be added to form the slurry in the preferred amounts.

These amounts may of course be varied, but have been found to be optimal for the purpose intended. The sodium sulfite is provided in an approximately stoichiometric amount, even though it may be in excess after the calcium hypochlorite has previously degraded or reacted. It is best practice to be certain that all of it has been reacted.

Other advantages of this invention become evident with its use. Many sharps have hollow cavities or passages, such as needles and barrels. It is most desirable for these to be filled, even though they are sometimes of near capillary dimensions. In fact the cementitious material expands as it starts to set. It tends to flow readily into the spaces and lumens, assisted by the forces of capillary action and of expansion of the mass. This is a secondary and useful functional feature.

Furthermore, the alkalinity of this composition further inhibits any organisms which might somehow have survived the hypochlorite.

This invention is not to be limited by the embodiment shown in the drawings and described in the description, which is given by way of example and not of limitation, but only in accordance with the scope of the appended claims.

We claim:

1. A kit for interim sanitary storage and subsequent permanent inurnment of medical sharps comprising:

a receptacle comprising an impermeable wall forming an enclosed cavity, a port through said wall, an externally threaded receptacle neck around the port, and a receptacle closure cap removably engageable to said receptacle neck and a means to lock for permanently engaging said receptacle closure cap to said receptacle neck, to permanently close said receptacle port;

a quantity of dry calcium hypochlorite in said receptacle cavity, occupying only a portion of the volume of said receptacle cavity;

a supply container comprising an impermeable wall forming an enclosed cavity, a supply container port through said wall, an externally threaded supply container neck, a supply container closure cap engageable to said supply container neck;

a quantity of dry sodium sulfite, dry portland cement, and dry pumice in said supply container cavity, said sodium sulfite, portland cement and pumice occupying only a portion of said supply container cavity;

whereby medical sharps may be inserted into the receptacle cavity there to be contacted by said calcium hypochlorite and by gases emitted from said calcium hypochlorite, and microorganisms associated with the sharps may be destroyed thereby;

whereby water can be poured into the supply container to form a slurry with its dry contents; and whereby the slurry can be poured into the receptacle cavity, and the receptacle closure cap permanently closed by said means to lock, the receptacle shaken, the combined materials thereafter curing to a solid mass in which the sharps are encapsulated, the chemicals are reduced, and the receptacle can be disposed of in a non-hazardous landfill.

2. A combination according to claim 1 in which potassium chloride is added to the materials in the supply container.

3. A combination according to claim 1 in which the receptacle is provided with a reference line to indicate the maximum level of sharps and in which the supply container is provided with a reference line to indicate the desired level of water to be added to form the slurry.

4. A combination according to claim 1 in which sodium sulfite is provided in an amount which will reduce substantially all of the calcium hypochlorite which exists when the slurry is to be added, and in which the pumice and portland cement are provided in amounts which will cure to form a solid matrix for the sharps.

5. The process of destroying microorganisms on used medical sharps and later encapsulating said sharps in a cementitious body, said process comprising:

utilizing a receptacle comprising a wall forming an enclosed cavity, a receptacle port, an externally threaded receptacle neck around the receptacle port, and a receptacle closure cap engageable to said receptacle neck;

placing a quantity of dry calcium hypochlorite in said receptacle cavity, occupying only a portion of the volume of said receptacle cavity;

utilizing a supply container comprising a wall forming an enclosed cavity, a supply container port, an externally threaded supply container neck, and a supply container closure cap engageable to said supply container neck;

placing a quantity of dry sodium sulfite, dry portland cement, and dry pumice in said supply container cavity, said sodium sulfite, portland cement and pumice occupying only a portion of said supply conduit cavity;

placing medical sharps in the receptacle cavity and in contact with the calcium hypochlorite and with gases emitted by said calcium hypochlorite and closing the respective receptacle closure cap for interim storage of said medical sharps;

pouring water into said supply container and shaking it to form a slurry; and pouring said slurry into said receptacle, closing the receptacle with the receptacle closure cap and shaking it, the combined materials thereafter curing to a cementitious solid mass in which the sharps are encapsulated.

6. A process according to claim 5 in which a permanent lock is thereafter applied to said receptacle closure cap on said receptacle to prevent future entry to or leakage from said port of said receptacle.

* * * * *